US010265469B2

(12) United States Patent
Lee et al.

(10) Patent No.: US 10,265,469 B2
(45) Date of Patent: Apr. 23, 2019

(54) COMPENSATION DEVICE FOR SETTING FLOW RATE OF INFUSION SOLUTION, DEVICE FOR AUTOMATICALLY CONTROLLING FLOW RATE OF INFUSION SOLUTION, AND METHOD FOR CONTROLLING OPTIMAL TARGET FLOW RATE USING FLOW RATE COEFFICIENT OF FLOW RATE CONTROLLER

(71) Applicants: Dooyong Lee; HANVIT MD CO., LTD, Dunsan-ro, Seo-gu, Daejeon (KR)

(72) Inventors: Dooyong Lee, Daejeon (KR); Poomin Park, Daejeon (KR)

(*) Notice: Subject to any disclaimer, the term of this patent is extended or adjusted under 35 U.S.C. 154(b) by 263 days.

(21) Appl. No.: 15/023,956

(22) PCT Filed: Feb. 27, 2014

(86) PCT No.: PCT/KR2014/001633
§ 371 (c)(1),
(2) Date: Mar. 22, 2016

(87) PCT Pub. No.: WO2015/023036
PCT Pub. Date: Feb. 19, 2015

(65) Prior Publication Data
US 2016/0256628 A1 Sep. 8, 2016

(30) Foreign Application Priority Data

Aug. 16, 2013 (KR) .................. 10-2013-0097041

(51) Int. Cl.
G05D 7/06 (2006.01)
A61M 5/168 (2006.01)
A61M 5/172 (2006.01)

(52) U.S. Cl.
CPC ........ A61M 5/172 (2013.01); A61M 5/16877 (2013.01); A61M 5/16881 (2013.01);
(Continued)

(58) Field of Classification Search
CPC .............. A61M 5/172; A61M 5/16877; A61M 5/16881; A61M 5/16886; A61M 2205/52;
(Continued)

(56) References Cited

U.S. PATENT DOCUMENTS

| 6,280,408 B1* | 8/2001 | Sipin ................... A61M 5/1483 604/65 |
| 2007/0053513 A1* | 3/2007 | Hoffberg ............ G06K 9/00369 380/201 |
| 2012/0330279 A1* | 12/2012 | Tsabari ................ A61M 5/1411 604/518 |

FOREIGN PATENT DOCUMENTS

| JP | 11-319083 | 11/1999 |
| JP | 2010-145334 | 7/2010 |

(Continued)

OTHER PUBLICATIONS

English translation of 10-2011-0078483.
(Continued)

*Primary Examiner* — Ziaul Karim
(74) *Attorney, Agent, or Firm* — Antonio Ha & U.S. Patent, LLC

(57) ABSTRACT

The present invention relates to a compensation device for setting a flow rate of an infusion solution, a device for automatically controlling the flow rate of the infusion solution, and a method for controlling an optimal target flow rate using a flow rate coefficient of a flow rate controller, the compensation device adjusting a display scale of an infusion solution flow rate controller corresponding to a target flow rate on the basis of a one-time actually measured flow rate in setting the target flow rate by controlling an infusion solution flow rate controller of an infusion solution.

2 Claims, 9 Drawing Sheets

(52) U.S. Cl.
CPC ....... *A61M 5/16886* (2013.01); *G05D 7/0617* (2013.01); *G05D 7/0635* (2013.01); *A61M 2205/3306* (2013.01); *A61M 2205/52* (2013.01); *A61M 2205/70* (2013.01)

(58) Field of Classification Search
CPC ...... A61M 2205/3306; A61M 2205/70; G05D 7/0617; G05D 7/0635
USPC .......................................................... 700/282
See application file for complete search history.

(56) References Cited

FOREIGN PATENT DOCUMENTS

| KR | 10-0461947 | 12/2004 |
| KR | 10-2011-0078483 | 7/2011 |
| KR | 10-1058539 | 8/2011 |

OTHER PUBLICATIONS

English translation of 10-0461947.
English translation of 10-1058539.
English abstract of 2010-145334.
English abstract of 11-319083.

\* cited by examiner

[Fig. 1] Prior Art
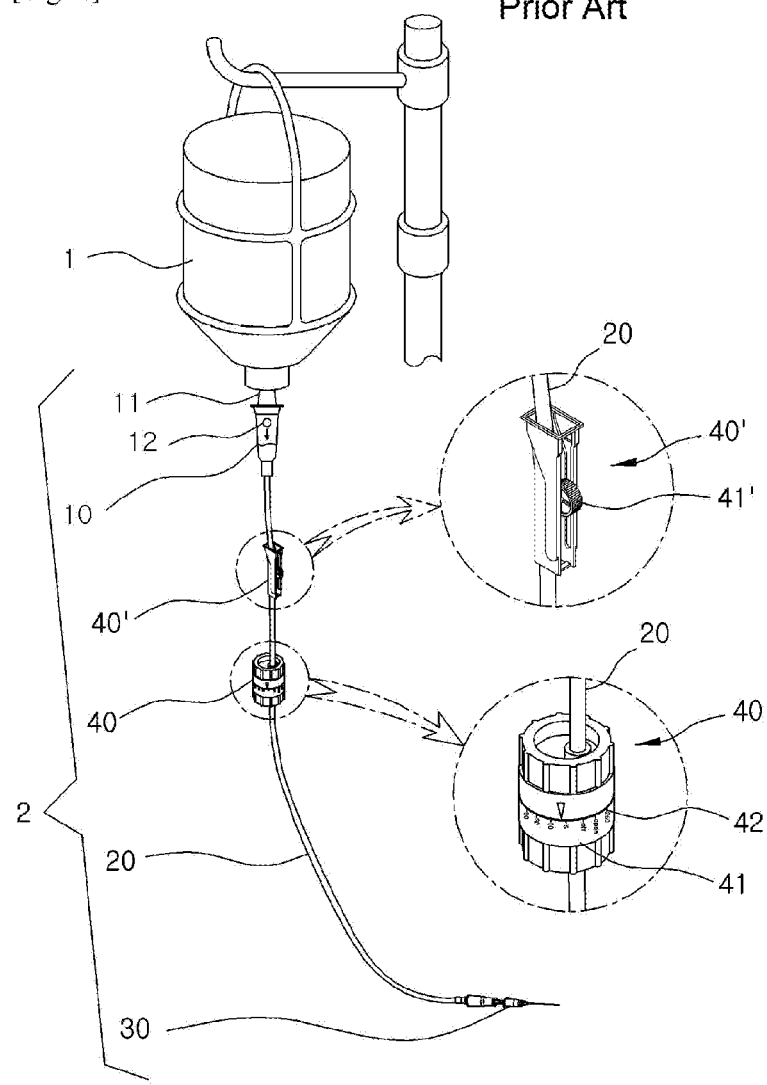
[Fig. 2] Prior Art
(a) (b)
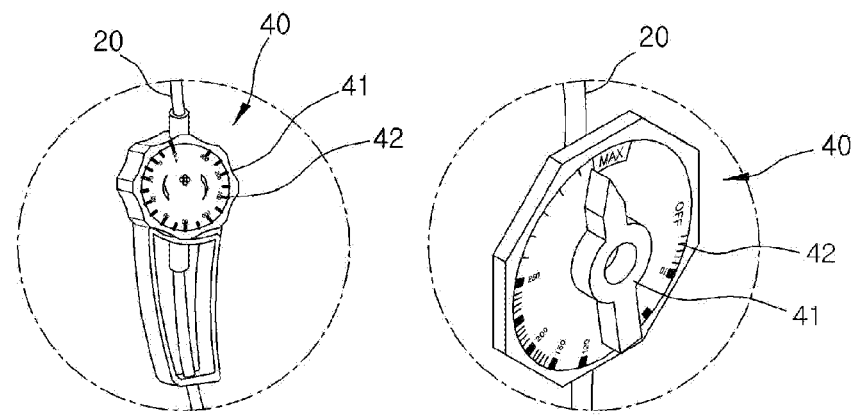

[Fig. 3]
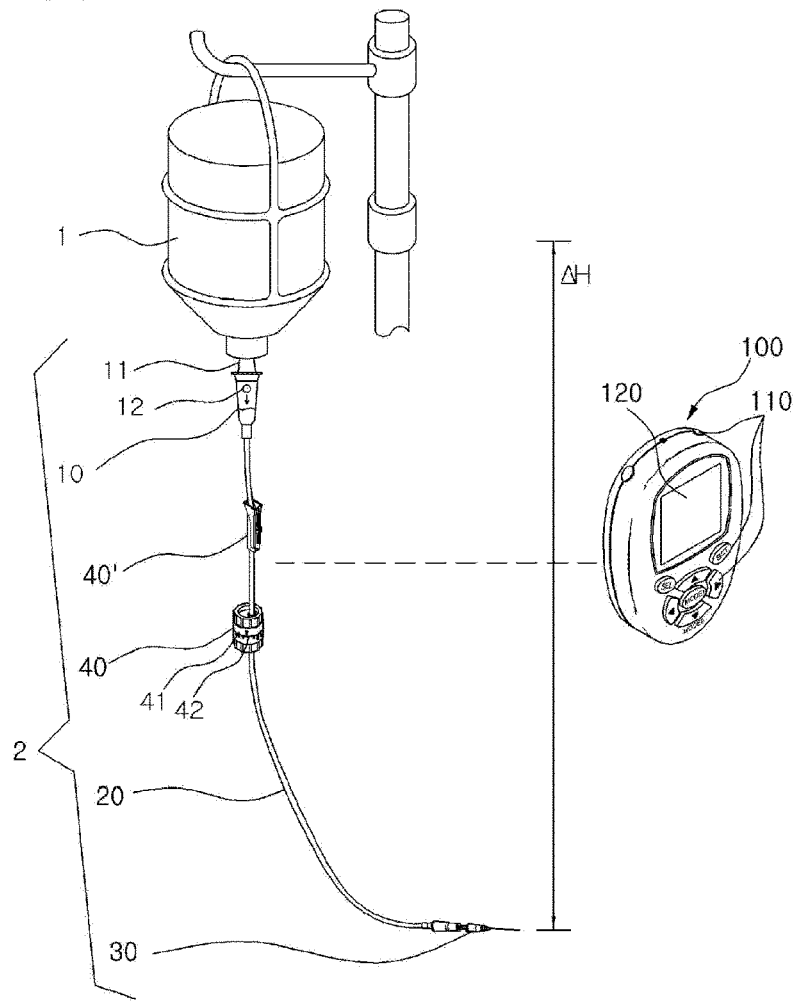
[Fig. 4]
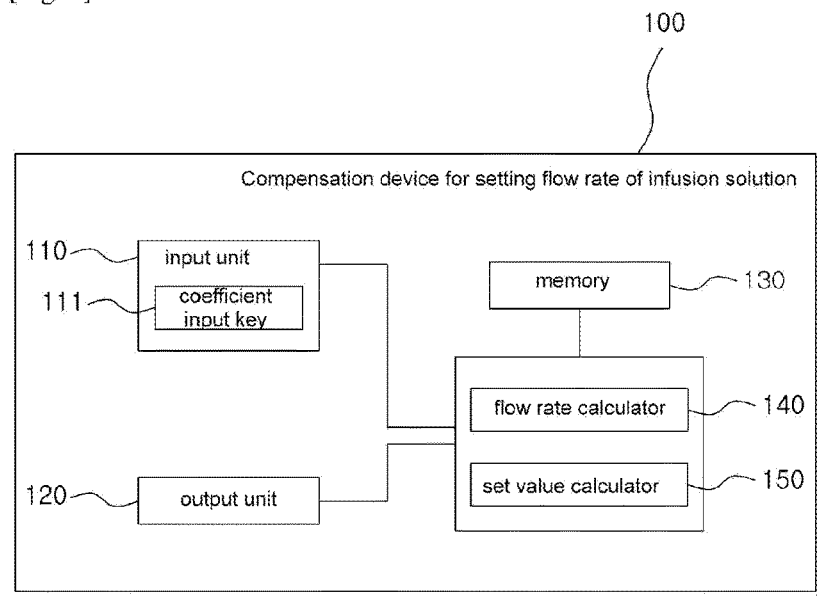

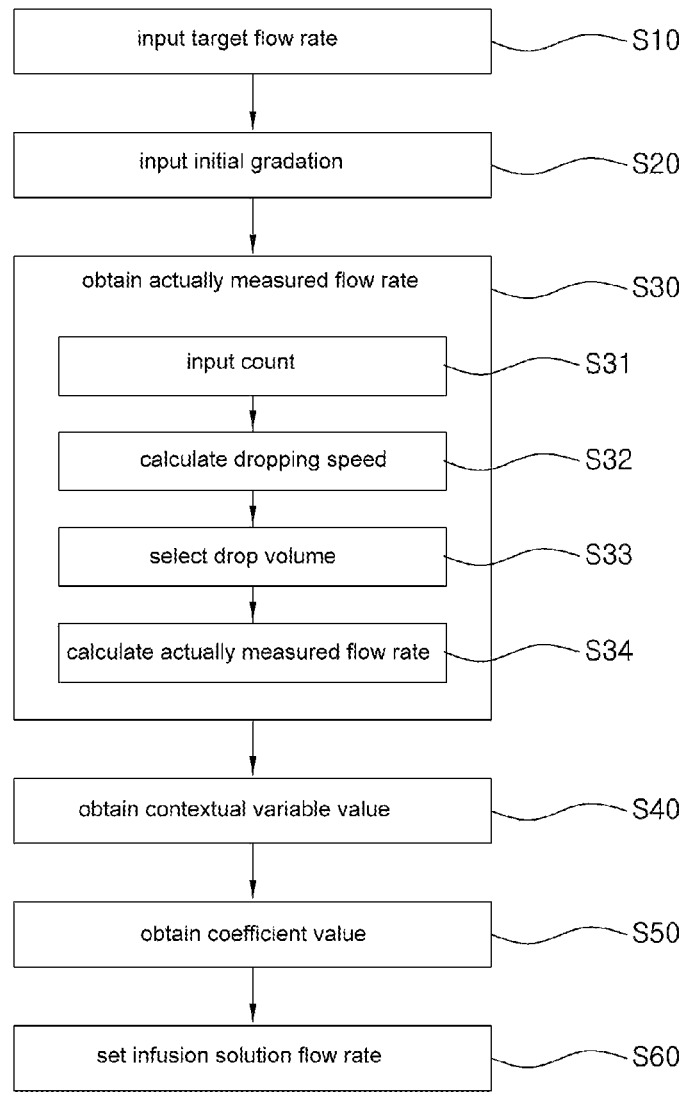
[Fig. 5]

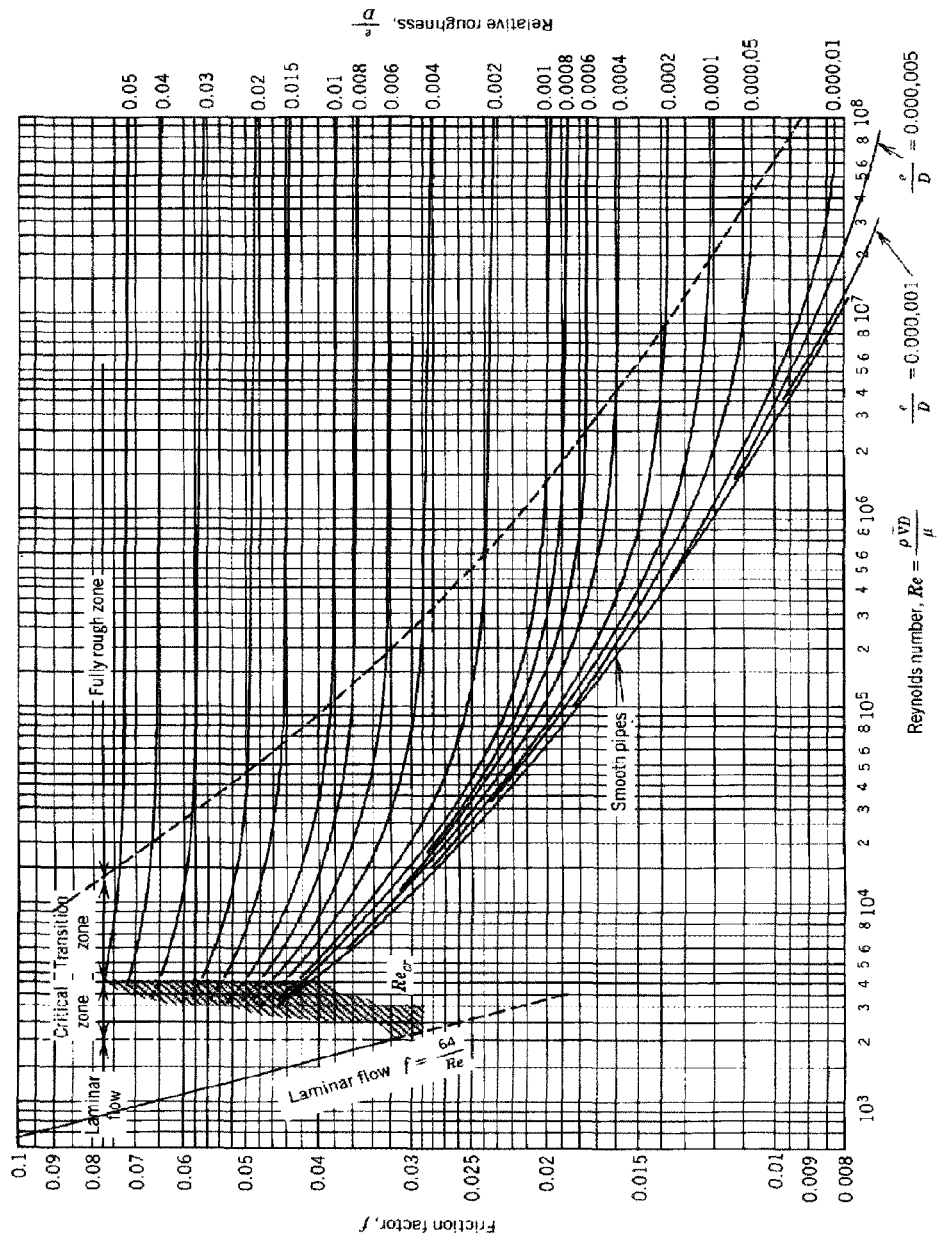
[Fig. 6]

[Fig. 7]
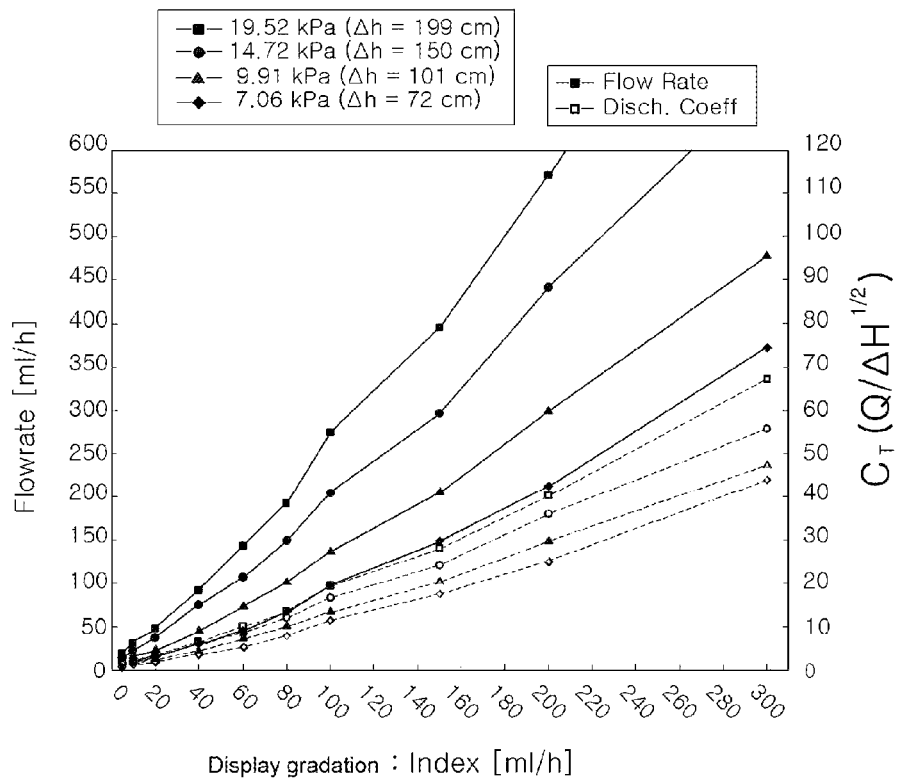
[Fig. 8]
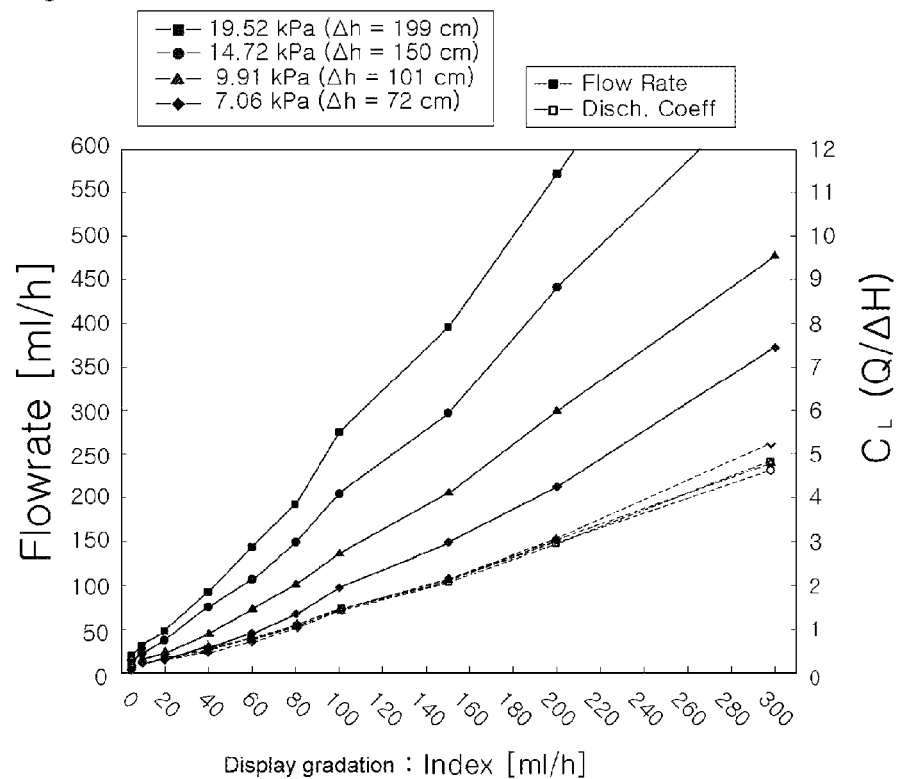

[Fig. 9]
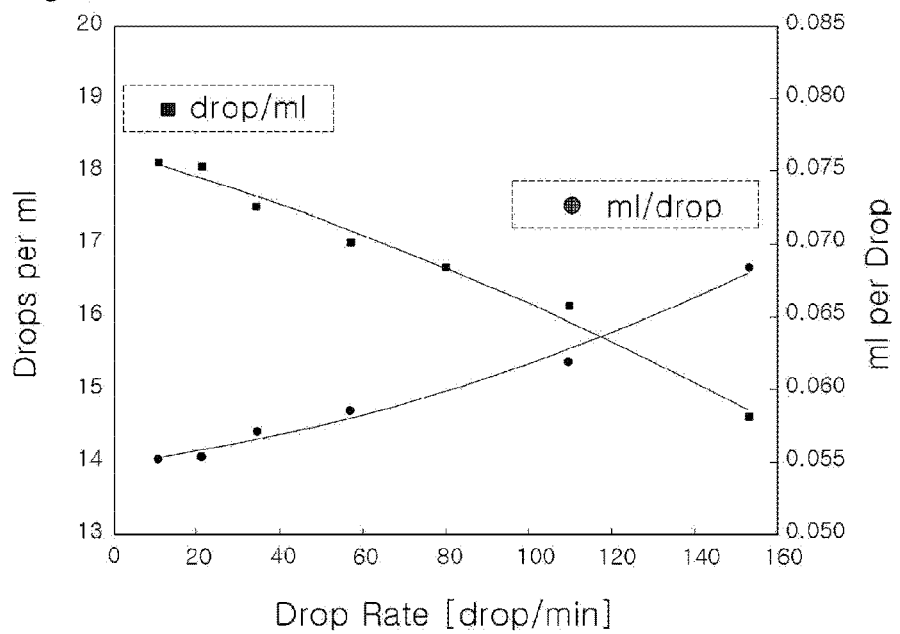
[Fig. 10]
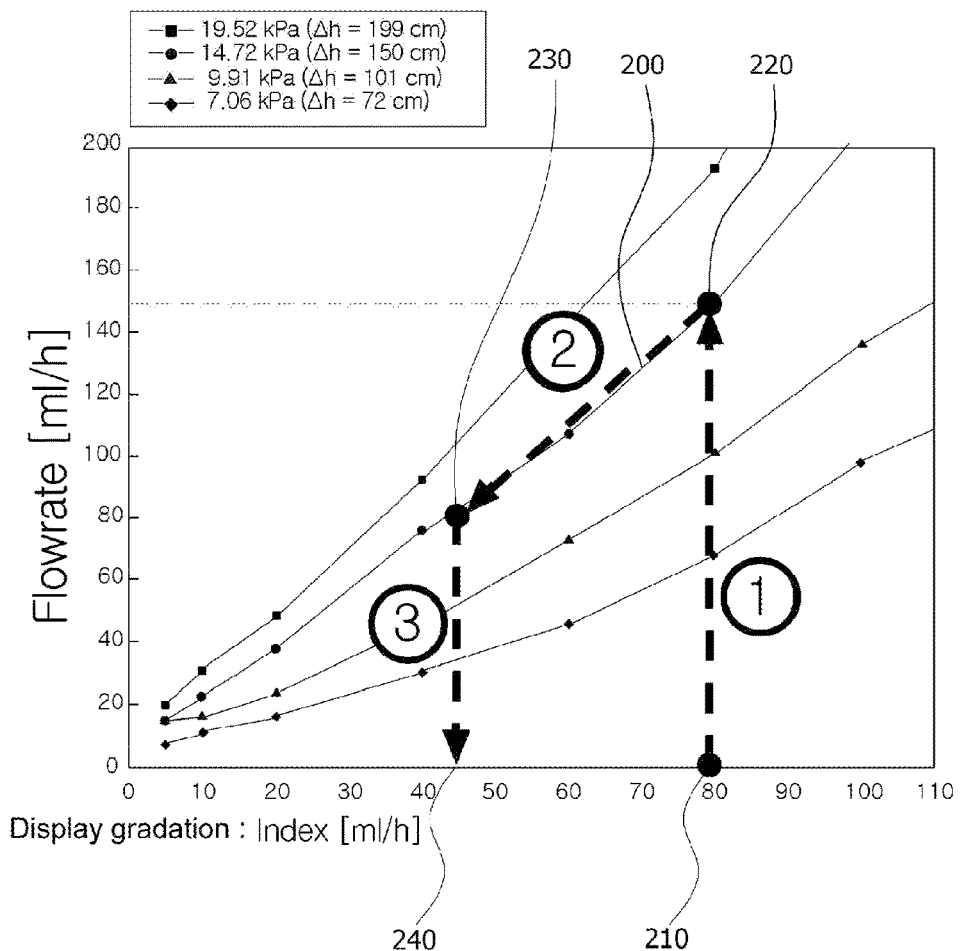

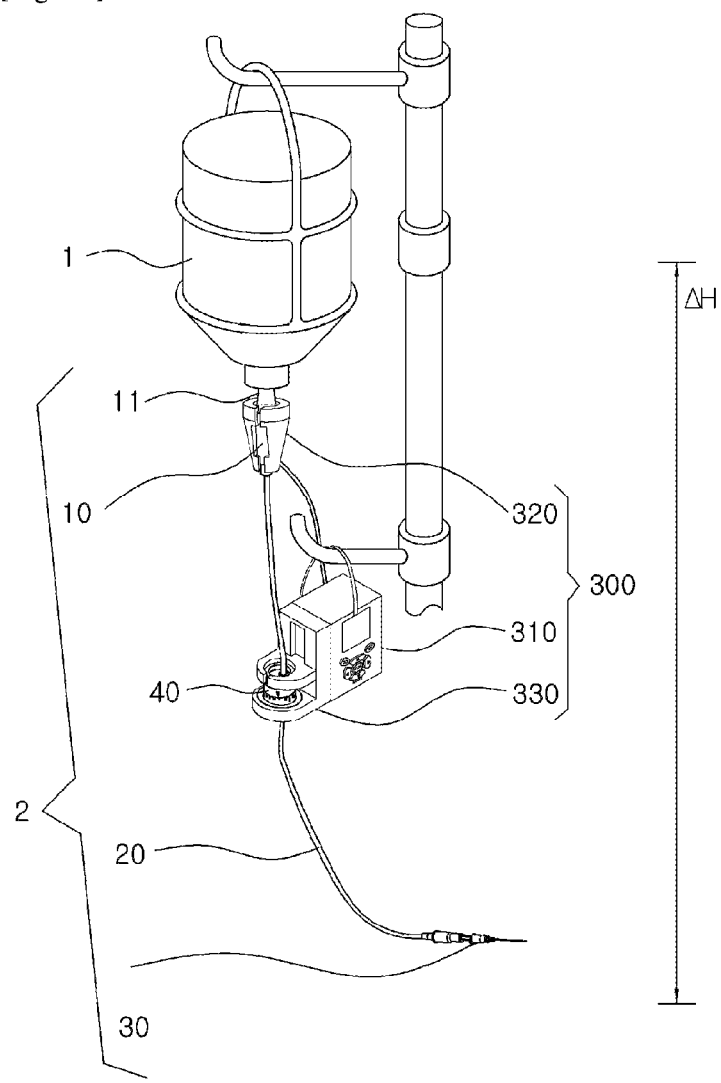
[Fig. 11]

[Fig. 12]
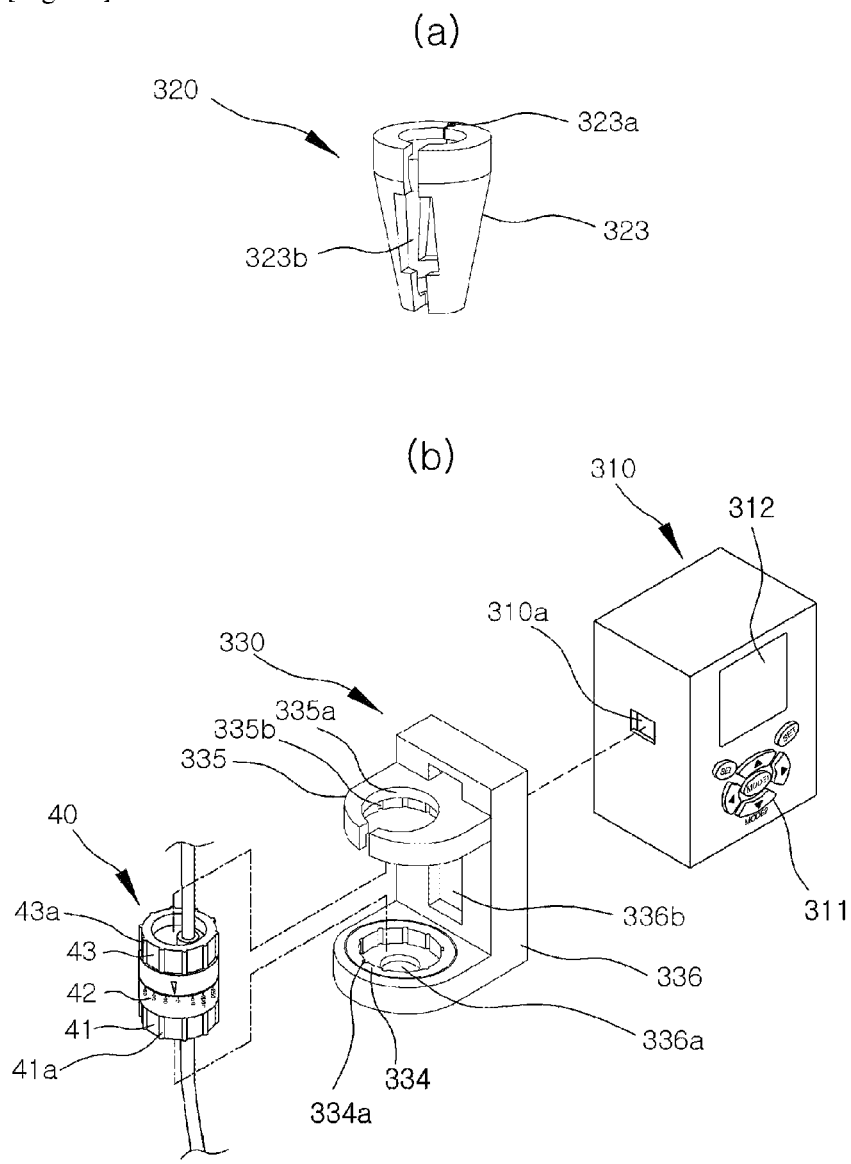

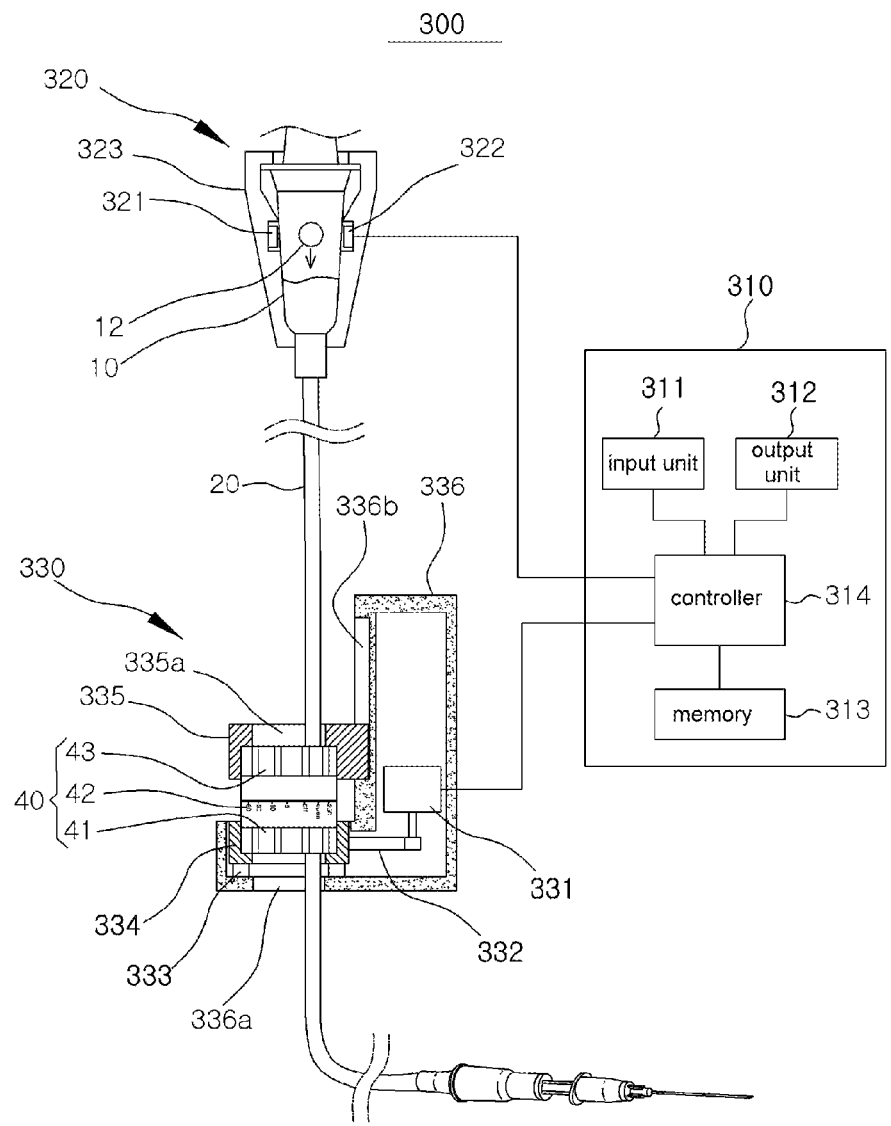
[Fig. 13]

COMPENSATION DEVICE FOR SETTING FLOW RATE OF INFUSION SOLUTION, DEVICE FOR AUTOMATICALLY CONTROLLING FLOW RATE OF INFUSION SOLUTION, AND METHOD FOR CONTROLLING OPTIMAL TARGET FLOW RATE USING FLOW RATE COEFFICIENT OF FLOW RATE CONTROLLER

TECHNICAL FIELD

The present invention relates to a compensation device for setting a flow rate of an infusion solution, a device for automatically controlling the flow rate of the infusion solution, and a method for controlling an optimal target flow rate using a flow rate coefficient of a flow rate controller, the compensation device adjusting a display scale of an infusion solution flow rate controller corresponding to a target flow rate on the basis of a one-time actually measured flow rate in setting the target flow rate by controlling an infusion solution flow rate controller of an infusion solution. More particularly, the present invention relates to a compensation device for setting a flow rate of an infusion solution, a device for automatically controlling the flow rate of the infusion solution, and a method for controlling an optimal target flow rate using a flow rate coefficient of a flow rate controller, the compensation device obtaining a display scale of an infusion solution flow rate controller for a target flow rate after estimating the installation condition of an infusion solution, set through a one-time actually measured flow rate, on the basis of fluctuation information of the flow rate according to change in the installation condition of the infusion solution set and the position of the display scale of the infusion solution flow rate controller, by classifying a factor affecting the flow rate as the position of the display scale of the infusion solution flow rate controller and the installation condition of the infusion solution set.

BACKGROUND ART

FIG. 1 is a view illustrating an installation condition of a typical infusion solution set, and FIG. 2 is a view illustrating various types of infusion solution flow rate controllers for controlling the flow rate of infusion solution in a commercially available infusion solution.

Treatment using an infusion solution is carried out by connecting an infusion solution bottle 1 to an infusion solution set 2 and applying the water pressure coming from the difference in height between the infusion solution bottle 1 and the injection needle 30 to administer the infusion solution contained in the infusion solution bottle 1 to the patient through the injection needle 30 of the infusion solution 2.

The infusion solution set 2 connected with the infusion solution bottle 1 includes a insertion needle 11 at an upper portion thereof, which is inserted through the sealing cap of the infusion solution bottle 1 to allow the infusion solution to flow out of the infusion solution bottle 1, a dropping container 10 allowing the infusion solution flowing out through the insertion needle 11 to drop to an inner space thereof in the form of drops (unit: gtt) to collect in a lower portion of the inner space and then discharge, the injection needle 30 inserted into the patient's vein, a tube 20 connecting the dropping container 10 with the insertion needle 30 and functioning as a pathway for injecting the infusion solution, and an infusion solution flow rate controller 40 and roller clamp 40' provided at a middle of the tube 20 to control the flow rate of infusion solution.

The drop 12 falls in the inside of the dropping container 10 in the form of a water drop. The dropping container 10 is manufactured to have a predetermined volume as possible. For example, when manufactured to discharge 20 drops per 1 cc of infusion solution, the volume of one drop is ¹⁄₂₀ cc, and when manufactured to discharge 60 drops per 1 cc of infusion solution, the volume of one drop is ¹⁄₆₀ cc. Accordingly, the flow rate of infusion solution injected through the infusion solution set 2 may be calculated by measuring the period at which the drop falls inside the dropping container 10.

A target flow rate prescribed in an actual clinic may be adjusted by measuring the number of drops considering all other factors (height or type of infusion solution, thickness of injection needle, patient vascular resistance, etc.) than the infusion solution flow rate controller and positioning the flow rate controlling means based on the measured number.

Here, as the flow rate controlling means installed in the infusion solution set, there are the roller clamp 40' and the infusion solution flow rate controller 40 according to the shape of the adjusting part and the principle of controlling flow rate. The roller clamp 40' varies the cross-sectional area of flow path of the tube 20 by moving up and down a manipulating unit 41' constituted of rollers. The roller clamp 40' determines the maximum and minimum speed by a small degree of spacing control and thus has difficulty in controlling and marking exact gradations.

In order to compensate for such shortcomings of the roller clamp 40', the infusion solution flow rate controller 40 (also referred to as an IV flow regulator) has been recently developed that controls the flow rate by varying internal flow paths as shown in FIG. 1 or 2. The infusion solution flow rate controller 40 may vary flowrates by rotating the manipulating unit 41 to change rotation angles. The infusion solution flow rate controller 40 has display gradations 42 marked within a rotation angle adjustment range and may be adjusted to a display gradation 42 fitting the target flow rate to adjust the flow rate.

As shown in FIG. 1, the infusion solution set with the infusion solution flow rate controller 40 generally uses the roller clamp 40' as well.

In the clinic, however, the flow rate of infusion solution administered and measured by the infusion solution set 2 shows a substantial difference from the display gradation 42. This is why the display gradation 42 of the infusion solution flow rate controller 40 has been marked based on the result obtained by performing a test using one type of infusion solution at a predetermined height in the lab without considering factors actually influencing the speed of infusion solution (e.g., height or type of infusion solution, thickness of injection needle, and patient's vascular resistance). The actual clinical site reveals significant differences from the lab. Most of all, since the lab does not consider the patient's vascular resistance (which varies for each of children, young people, or elderly people), prescribing the speed depending on the speed displayed is very critical in treating the patient, and a significant difference between prescribed flow rate and actually administered flow rate may put the patient in high risk.

According to Applicant's Korean Patent No. 10-1058539, a reference point is set when marking a display gradation 42 in an infusion solution flow rate controller 40, and a relative ratio between the flow rate at the display gradation and the flow rate at the reference point is marked as a display gradation so that a target flow rate of infusion solution may be administered only by measuring the flow rate at the reference point and then adjusting to the display gradation fitting the ratio with the target flow rate. According to this, since the target flow rate may be adjusted by the flow rate actually measured only once, the display gradation fitting the target flow rate may be quickly discovered.

However, currently available infusion solution flow rate controllers adjust the flow rate by varying the depth of circular flow path, so that the flow pattern according to the variation in display gradation is not linear.

In Korean Patent No. 10-1058539, the infusion solution flow rate controller needs to be a linear system in order to display gradations of the infusion solution flow rate controller with relative ratios, and this is pricey and pose limitations on commercial use.

Further, since the display gradations of the infusion solution flow rate controller are marked with ratios upon correction speed, the reference point of the infusion solution flow rate controller should always be fixed at the same position when measuring the flow rate once in order to discover a display gradation fitting the target flow rate, and the position of the flow rate controller should be moved back to the reference point even upon speed correction during the infusion solution treatment.

Further, since the speeds are indicated with ratios, it differs from the actual display unit gradation that is conventionally used and thus leads to difficulties in intuitive use and changing custom.

SUMMARY

Objects

Accordingly, an object of the present invention is to provide a compensation device, automatic infusion solution flow rate controller, and method for adjusting the optimal target flow rate using a flow rate coefficient of a flow rate controller, which, even when the installation state of the infusion solution set is varied, may allow for quick and precise discovery of the adjusted position of the infusion solution flow rate controller fitting the target flow rate by reflecting the variation, together with increased accuracy of flow rate by reflecting a variation in drop volume.

[Configuration]

To achieve the above object, there is provided a compensation device for setting a flow rate of an infusion solution, obtaining a display gradation to be indicated by a manipulating unit 41 to administer a target flow rate of the infusion solution according to a prescription of infusion solution treatment in an infusion solution set 2 including an infusion solution flow rate controller 40 having display gradations marked within a manipulation range of the manipulating unit 41 to allow for adjustment of the flow rate of the infusion solution as a display gradation indicated by the manipulating unit 41 is varied, the compensation device comprising: an input unit 110 for obtaining an initial gradation indicated by the manipulating unit 41 and an actually measured flow rate obtained by performing measurement while the manipulating unit 41 indicates the initial gradation; a memory 130 storing a value for a coefficient C for each display gradation obtained by putting measured values of a contextual variable X and a flow rate Q in a preset equation among a measurable contextual variable X varying depending on an installation state of the infusion solution set 2, a coefficient C varying the display gradation indicated by the manipulating unit 41, and a flow rate Q of the infusion solution administered through the infusion solution set 2; a set value calculator 150 putting a value $C_1$ of the coefficient C corresponding to the initial gradation and the actually measured flow rate in the equation to obtain a value $X_1$ of the contextual variable X and then putting the obtained value $X_1$ of the contextual variable X and the target flow rate in the equation to obtain a value $C_2$ of the coefficient C; and an output unit 120 outputting a display gradation corresponding to the value $C_2$ of the coefficient C obtained by the set value calculator 150.

The equation is $Q=CX$ which indicates that the flow rate Q is proportional to each of the contextual variable X and the coefficient C.

The contextual variable X is a difference in water level between an infusion solution bottle 1 and an injection needle 30 determined depending on the installation state of the infusion solution set 2.

The contextual variable X is a difference in height between an infusion solution bottle 1 and an injection needle 30 determined depending on the installation state of the infusion solution set 2.

Effects of the Invention

The present invention configured as above may previously obtain the equation using, as variables, a factor for installation state of the infusion solution set affecting the flow rate of infusion solution administered through the infusion solution set and a factor for adjusting display gradations of the infusion solution flow rate controller and a factor according to the adjusting display gradation of the infusion solution flow rate controller to allow for discovery of an exact target gradation fitting the installation state with the flow rate actually measured only once at some display gradation, thus enabling quick and exact adjustment of flow rate.

The present invention may be configured in a portable device to store the factor according to the adjusting gradation of the infusion solution flow rate controller, so that flow rate adjustment performed by various types of infusion solution flow rate controllers may be carried out by such a single portable device.

BRIEF DESCRIPTION OF DRAWINGS

FIG. 1 is a view illustrating a typical infusion solution set.

FIG. 2 is a view illustrating another type of infusion solution flow rate controller for controlling the flow rate of infusion solution in a commercial infusion solution set.

FIG. 3 is a view illustrating a state of using a compensation device for setting an infusion solution flow rate according to an embodiment of the present invention.

FIG. 4 is a block diagram illustrating a compensation device for setting an infusion solution flow rate according to an embodiment of the present invention.

FIG. 5 is a flowchart illustrating a method for adjusting an optimal target flow rate using a flow rate coefficient of a flow rate controller according to an embodiment of the present invention.

FIG. 6 illustrates a moody chart.

FIG. 7 is a graph illustrating a variation in flow rate for display gradations in an infusion solution flow rate controller and an overall flow rate coefficient for the display gradations.

FIG. 8 is a graph illustrating a variation in flow rate for display gradations in an infusion solution flow rate controller and a laminar flow overall flow rate coefficient for the display gradations.

FIG. 9 is a graph illustrating a variation in drop volume for dropping speed.

FIG. 10 is a flow rate graph for the display gradation illustrating an example of actual application of a method for adjusting an optimal target flow rate using a flow rate coefficient of a flow rate controller according to an embodiment of the present invention.

FIG. 11 is a view illustrating a state of using an automatic infusion solution flow rate controller according to an embodiment of the present invention.

FIG. 12(a) is a perspective view illustrating the flow rate sensor 320 FIG. 11. FIG. 12(b) is a perspective view illustrating the electromotive device 330 of FIG. 11.

FIG. 13 is a view illustrating a configuration of an automatic infusion solution flow rate controller according to an embodiment of the present invention.

DESCRIPTION OF EXEMPLARY EMBODIMENTS

Hereinafter, preferred embodiments of the present invention are described with reference to the accompanying drawings to be easily practiced by one of ordinary skill in the art.

<Compensation Device for Setting Infusion Solution Flow Rate>

FIG. 3 is a view illustrating a state of using a compensation device for setting an infusion solution flow rate according to an embodiment of the present invention. FIG. 4 is a block diagram illustrating a compensation device for setting an infusion solution flow rate according to an embodiment of the present invention.

Referring to FIGS. 3 and 4, according to an embodiment of the present invention, the compensation device 100 for setting an infusion solution flow rate is a device connecting an infusion solution set 2 to an infusion solution bottle 1 to adjust the flow rate of infusion solution to be administered to a target flow rate determined according to a prescription of infusion solution treatment.

Here, as described in connection with FIGS. 1 and 2, the infusion solution set 2 has a known configuration including a dropping container 10, a tube 20, an injection needle 30, and an infusion solution flow rate controller 40 and thus is briefly described.

The dropping container 10 inserts an insertion needle 11 through a cap covering the infusion solution bottle 1 to allow the infusion solution to flow out from the infusion solution bottle 1 through the insertion needle 11 and allowing the infusion solution flowing out through the insertion needle 11 from the internal space to fall in the form of drops 12 and to flow to the tube 20 while maintaining a predetermined water level in a lower portion of the internal space.

The injection needle 30 is inserted to the patient's vein. The tube 20 connects the dropping container 10 with the injection needle 30 so that the infusion solution is administered through the injection needle 30.

The infusion solution flow rate controller 40 is installed around the tube 20 to adjust the flow rate of infusion solution flowing through the tube 20 by moving the manipulating unit 41. There are various types of the infusion solution flow rate controller 40. According to an embodiment of the present invention, the infusion solution flow rate controller 40 has gradations marked thereon within a range of manipulating of the manipulating unit 41 so that the flow rate of infusion solution is adjusted by changing the gradations indicated by the manipulating unit 41.

As described above, in connecting the infusion solution bottle 1 to the infusion solution set 2 to administer the infusion solution to the patient, the present invention obtains and outputs a gradation that should be indicated by the manipulating unit 41 in the infusion solution flow rate controller 40 to administer the infusion solution in the target flow rate, and for the purposes, includes an input unit 110, an output unit 120, a memory 130, a flow rate calculator 140, and a set value calculator 150.

The input unit 110 is provided to obtain a target flow rate determined according to a prescription of infusion solution treatment, any initial gradation indicated by the manipulating unit 41 of the infusion solution flow rate controller 40, and an actually measured flow rate that is a flow rate obtainable by performing measurement while the manipulating unit 41 of the infusion solution flow rate controller 40 indicates the initial gradation. Here, the target flow rate and the initial gradation are received as values. The actually measured flow rate may be obtained by measuring a dropping period of drop by other flow rate measurement device or in a scheme generally used in clinics while observing a clock and including a drop volume and may be input through the input unit 110. However, according to an embodiment of the present invention, the input unit 110 includes a coefficient input key 111 for counting drops, and the flow rate calculator 140 described below is provided. Thus, a flow rate is calculated by inputting a count of drops when the drops fall.

The output unit 120 outputs the position of a target gradation obtained by the set value calculator 150 described below. The target gradation indicates the position of a display 1o gradation that should be indicated by the manipulating unit 41 in the infusion solution flow rate controller 40 for administering a target flow rate of infusion solution. If the manipulating unit 41 is adjusted to the target gradation, the flow rate administered by the infusion solution set 2 is set to the target flow rate.

The memory 130 stores characteristic information on the infusion solution flow rate controller 40 and characteristic information on the dropping container 10.

The characteristic information on the infusion solution flow rate controller 40 is configured of a predetermined equation, $Q=f(C,X)$, indicating the relation between measurable contextual variable X varying depending on the installation state of the infusion solution set, coefficient C varied by changing the position of the display gradation indicated by the manipulating unit 41 in the infusion solution flow rate controller, and flow rate Q administered by the infusion solution set. That is, flow rate Q is represented as a function varied depending on contextual variable X and coefficient C. Here, contextual variable X and coefficient C are allowed to be orthogonal with each other so that even when contextual variable X varies, coefficient C does not. The orthogonality may be shown below from the process of deriving the equation $Q=f(C,X)$ for the infusion solution flow rate controller.

The coefficient C for each display gradation is obtained by actually measuring contextual variable X and flow rate Q at each display gradation and replacing them in equation $Q=f(C,X)$ and is then stored together in the memory 130. Specifically, flow rate Q is measured while changing the installation state (i.e., contextual variable X) of infusion solution set at each display gradation 42, and the contextual variable X and flow rate Q as measured are input to the equation $Q=f(C,X)$ to obtain coefficient C. In this way, the coefficient C for each display gradation 42 is obtained. If the coefficient C obtained per contextual variable X at each display gradation 42 is difficulty to exhibit exact consistency due to experimental errors, the coefficients C obtained by varying the installation state at each display gradation are averaged to the coefficient C for the display gradation.

Meanwhile, the coefficient C for between display gradations 42 may be estimated using a close value, or a function of a curved line that is obtained by performing curve fitting on the coefficient C, that is, a function of coefficient C for the display gradation may be stored in the memory 130 for use, and such is a modification of a scheme of storing and utilizing data and obviously does not depart from the scope of the present invention.

According to an embodiment of the present invention, the contextual variable X is determined as a water level difference varying depending on the installation state of the infusion solution set, i.e., a difference in height between the infusion solution bottle 1 and the injection needle 30 or a water pressure difference, i.e., a difference in water pressure between the infusion solution bottle 1 and the injection needle 30. Here, the difference in height may be taken as the water level difference. The water level of the infusion solution bottle decreases as the infusion solution is administered, and thus, the water level difference gradually reduces. However, an error caused as the water level reduces may be considered to be within a tolerance range allowable upon infusion solution treatment in applying the present invention. Accordingly, according to the present invention, the difference in height is interchangeably used with the water level difference.

Further, according to an embodiment of the present invention, different equations $Q=f(C,X)$ are selected depending on whether the flow of infusion solution administered through the infusion solution bottle 1 is turbulent flow or laminar flow, and if laminar flow, the coefficient C becomes a laminar flow overall flow rate coefficient, and if turbulent flow, the coefficient C becomes an overall flow rate coefficient. Current commercial infusion solutions 1 are determined to present laminar flows as described below. Thus, the equation $Q=CX$ is adopted for the current commercial infusion solution 1.

Further, as the flow rate Q in the equation $Q=f(C,X)$, a flow rate obtained from the dropping speed described below may be used, but in this case, the drop volume varying depending on the dropping speed applies to the flow rate as described below.

Next, the characteristic information on the dropping container 10 is information on the drop volume set for each magnitude of dropping speed (number of drops per unit time: number of drops falling per unit time).

Generally, a value is previously set under the assumption that the volume of drop 12 falling in the internal space of the dropping container 10 is constant, and drops 12 are counted to calculate the flow rate. However, Applicant's result of actual measurement reveals that the volume of drop 12 varies depending on dropping speeds, and thus, an exact flow rate may be obtained by applying the volume of drop 12 corresponding to the dropping speed. That is, the flow rate of infusion solution in the infusion solution bottle 1 may be shown from the drop 12 falling in the dropping container 10. The volume of drop 12 is varied depending on the dropping speed, and thus, the flow rate is calculated by applying the drop volume corresponding to the dropping speed in the flow rate calculator 140.

The flow rate calculator 140, when a count input occurs in the coefficient input key 111 of the input unit 110, calculates a time difference of the count input (i.e., pressing the coefficient input key 111) to calculate the dropping speed (number of drops per unit time) and then multiplies the dropping speed with the drop volume to obtain the flow rate. Here, the obtained flow rate is the actually measured flow rate.

Since the drop volume varies depending on the dropping speed, the drop volume corresponding to the actually measured flow rate applies based on the characteristic information on the dropping container 10 as described above.

The set value calculator 150 calculates the target gradation based on the target flow rate and initial gradation received from the input unit 110 and the actually measured flow rate obtained from the flow rate calculator 140 and then outputs the target gradation through the output unit 120. Here, the target gradation is a display gradation at the position indicated by manipulating the manipulating unit 41 of the infusion solution flow rate controller 40 so that the flow rate of infusion solution becomes the target flow rate.

Specifically, the value $C_1$ of coefficient C corresponding to the inputted initial gradation and the obtained actually measured flow rate are input to the equation $Q=f(C,X)$ to obtain the value $X_1$ of contextual variable X, and the obtained contextual variable $X_1$ and the target flow rate are input to the equation $Q=f(C,X)$ to obtain a value $C_2$ of the coefficient C. The position of the display gradation corresponding to the obtained $C_2$ of coefficient C is output to the output unit 120 as the target gradation. That is, after the contextual variable, i.e., the installation state of infusion solution set, is obtained from the actually measured flow rate and initial gradation, the target gradation is found and output for obtaining the target flow rate in the installation state of infusion solution set.

Meanwhile, the display gradation 42 of the infusion solution flow rate controller 40 is typically marked as a flow rate, and if the flow rate is replaced with the coefficient C, the compensation device 100 for setting an infusion solution flow rate according to an embodiment of the present invention stores the position of each display gradation as coefficient C.

On the other hand, for the case where the display gradation 42 is marked as flow rate, if the compensation device 100 for setting an infusion solution flow rate according to an embodiment of the present invention is used to obtain an actually measured flow rate with the initial gradation when flow rate is actually measured consistent with the target flow rate, the initial gradation when the flow rate is actually measured may be rendered not to be received. This is why, in this case, the initial gradation value that should be received is consistent with the target flow rate.

<Method for Adjusting Optimal Target Flow Rate Using Flow Rate Coefficient of Flow Rate Controller>

FIG. 5 is a flowchart illustrating a method for adjusting infusion solution flow rate using a compensation device 100 for setting infusion solution flow rate as described above.

Referring to FIG. 5, according to an embodiment of the present invention, the method for adjusting the optimal target flow rate using the flow rate coefficient of the flow rate controller includes the step S10 of inputting a target flow rate, the step S20 of inputting initial gradation, the step S30 of obtaining an actually measured flow rate, the step S40 of obtaining a contextual variable, the step S50 of obtaining a coefficient, and the step S60 of setting an infusion solution flow rate.

In the target flow rate input step S10, a target flow rate determined according to a prescription of infusion solution treatment is received.

In the initial gradation input step S20, an initial gradation indicated by the manipulating unit 41 is received. Here, the received initial gradation is a display gradation indicated by the manipulating unit 41 of the infusion solution flow rate controller 40 when obtaining the actually measured flow rate described below. In using the infusion solution flow rate controller having flow rates as display gradations, if the actually measured flow rate is obtained after the manipulating unit 41 is manipulated to indicate the display gradation at the position where a flow rate consistent with the target flow rate is marked, according to an embodiment of the present invention, the infusion solution flow rate adjusting method does not include the initial gradation input step S20 and runs the target flow rate input step S10 and then the actually measured flow rate obtaining step S30, wherein the initial gradation is treated to be consistent with the target flow rate.

In the actually measured flow rate obtaining step S30, the flow rate is actually measured with the initial gradation indicated by the manipulating unit 41 of the infusion solution flow rate controller, thereby obtaining the actually measured flow rate. According to an embodiment of the present invention, the drops 12 are counted by the coefficient input key 111, and thus, the actually measured flow rate obtaining step S30 includes a count input step S31 of receiving a predetermined number of times of the count input, wherein the input of the coefficient input key 111 pressed whenever the drop 12 falls is taken as the count input, a dropping speed calculating step S32 of calculating a dropping speed (number of drops per unit time) from the time difference between count inputs, selecting a predetermined drop volume corresponding to the calculated dropping speed (S33), and an actually measured flow rate calculating step S34 of calculating an actually measured flow rate by multiplying the selected drop volume by the dropping speed. Here, the predetermined drop volume differs depending on the dropping speed as described above, and thus, it is set per magnitude of dropping speed and is selected as a value corresponding to the dropping speed obtained in the dropping speed calculating step S32. Meanwhile, the actually measured flow rate obtaining step S30 may adopt the method for measuring flow rate by the "infusion solution injection speed measuring device" disclosed in Applicant's Korean Patent No. 10-0706954 and also in this case, the drop volume corresponding to the dropping speed is selected.

Meanwhile, although according to an embodiment of the present invention in the count input step S31, drops 12 are counted and input by the coefficient input key 111, other component for counting drops 12 may be provided without the coefficient input key 111.

For example, the compensation device 100 for setting an infusion solution flow rate may be configured to include a u-shaped path enabling the dropping container 10 to be inserted therein, a light emission device provided at a side of the path, and a light receiving device provided at the other side of the path to sense light emitted from the light emission device as components for counting drops 12. Accordingly, the dropping container 10 is inserted into the path, and then, the light emission device emits light, and the light receiving device senses the light so that drops 12 are counted based on variations in the light sensed by the light receiving device. In other words, light emitted from the light emitting device passes through the dropping container 10 and is sensed by the light receiving device. Since the falling drop 12 disturbs the light (e.g., dispersion or reflection of the light), the fall of the drop 12 is sensed and counted based on whether the light is disturbed.

As another example, the compensation device 100 for setting an infusion solution flow rate may be configured to include a camera and an image processor as components for counting drops 12. In other words, the dropping container 10 is captured by the camera to produce an image, and the image is interpreted by the image processor to extract the image of the drop 12. Accordingly, drops 12 are counted by detecting the occurrence and fall of the image of the drop 12.

On the other hand, the count input step S31 and the dropping speed calculating step S32 are steps for obtaining the dropping speed, and thus, if other device is used to obtain the dropping speed and the components for the count input step S31 and the dropping speed calculating step S32 are not included in the compensation device 100 for setting an infusion solution flow rate, the dropping speed should be received by the input unit 110.

In the contextual variable obtaining step S40, the value $C_1$ of coefficient C corresponding to the initial gradation inputted in the initial gradation input step S20 and the actually measured flow rate obtained in the actually measured flow rate obtaining step S30 are input to the equation $Q=f(C,X)$ to obtain the value $X_1$ of contextual variable X. Here, the obtained value $X_1$ of the contextual variable X is a value indicating the installation state of the infusion solution set 2, and according to an embodiment of the present invention, it is a difference in water level or water pressure that occurs to a difference in height between the infusion solution bottle 1 and the injection needle 30.

In the coefficient obtaining step S50, the value $X_1$ of the contextual variable X obtained in the contextual variable obtaining step S40 and the target flow rate inputted in the target flow rate input step S10 are input to the equation $Q=f(C,X)$ to obtain the value $C_2$ of the coefficient C.

In the infusion solution flow rate setting step S60, the display gradation at the position corresponding to the value $C_2$ of the coefficient C obtained in the coefficient obtaining step S50 is output to the output unit 120 as the target gradation, so that the manipulating unit 41 of the infusion solution flow rate controller 40 is adjusted to fit the target gradation.

If, as the display gradation 42 of the infusion solution flow rate controller 40, the coefficient C at each display gradation, but not the flow rate, is marked, the value $C_2$ of the coefficient C obtained in the coefficient obtaining step S50 is output.

<Specific Embodiment of Equation $Q=f(C,X)$>

Hereinafter, specific embodiments of the equation $Q=f(C,X)$ are described.

First, major variables used in the equation are defined.

P: pressure, H: water level, Q: flow rate $\rho$: infusion solution density, $\mu$: viscosity coefficient, $\nu$: kinematic viscosity coefficient g: gravity acceleration, L: length of flow path, D: diameter of cross section of flow path A: cross-sectional area of flow path, V: flow speed, $V_1$: theoretical flow speed Re: Reynolds number, $c_a$: flow rate coefficient, f: friction factor, $C_T$: overall flow rate coefficient, $C_L$: laminar floor overall flow rate coefficient As shown in FIG. 3, the relation between the water pressure difference and pressure difference according to the difference in height between the infusion solution bottle 1 and the injection needle 30 is represented as in Equation 1 below, and thus, the water pressure difference may be represented with the water level difference.

$$\Delta P = \rho g \Delta H \qquad \text{Equation 1}$$

As shown in Equation 1 above, the pressure difference by the water level difference acts as a differential pressure to the front and rear ends of the flow rate controller to create a flow. Generally, the flow rate controller varies flow rates by adjusting the flow resistance against the differential pressure at the front and rear ends.

However, since the flow rate when infusion solution is administered has a very tiny value as compared with the use range of a general flow rate controller, it is difficult to perform precise flow rate adjustment with the general flow rate controller. That is, since the flow rate is very small, a significant flow of resistance is required to produce a high flow rate adjustment resolution.

The flow inside the flow path in a precise infusion solution flow rate controller is a sort of pipe flow. An equation representing the differential pressure by flow resistance in pipe flows is as shown in Equation 2 below (F. M. White, "Fluid Mechanics", $2^{nd}$ Ed., McGraw-Hill, 1986, ISBN 0-07-069673-X, p. 303, Eq. 6.30).

$$\Delta H = f \frac{L}{D} \frac{V^2}{2g} \qquad \text{Equation 2}$$

Here, the pressure loss is represented as water level difference, and f is the friction factor that may be obtained from a Moody chart shown in FIG. 6.

From Equation 2 above, as the diameter of the cross section of the flow path reduces or the length of flow path increases, a large flow resistance may be created. Using such relation, a narrow, long flow path is formed in the infusion solution flow rate controller, and an infusion solution is injected to an end of the flow path, and the point where the infusion solution is discharged is left to be varied along the flow path. Since the point where the infusion solution is discharged is varied by changing rotation angles of the manipulating unit 41, as the rotation angle of the manipulating unit 41 is changed, the length of the flow path is varied to change the flow resistance. Resultantly, although the differential pressure remains same at the front and rear ends of the infusion solution flow rate controller, the flow resistance is varied to lead to a change in the flow rate.

Since the hydromechanical variable representing the flow rate for the pressure at the front and rear ends of the flow rate controller is the flow rate coefficient, a change in the length of the flow path leads to a change in the flow rate coefficient of the flow rate controller. Flow rate coefficient (discharge coefficient) $c_d$ is represented as in Equation 3 below.

$$V = c_d V_i \qquad \text{Equation 3}$$

Here, the theoretical flow rate $V_i$ has the relation as shown in Equation 4 below for the front-rear end differential pressure, and from the same, Equation 3 above is represented as in Equation 5 below.

$$\Delta P = \frac{1}{2} \rho V_i^2 \qquad \text{Equation 4}$$

$$V = c_d \sqrt{\frac{2 \Delta P}{\rho}} \qquad \text{Equation 5}$$

By putting Equation 1 in Equation 5, the following Equation 6 for actual flow speed V may be obtained, and according to this equation, the flow speed is proportional to the square root of the water level difference.

$$V = c_d \sqrt{2g \Delta H} \text{ or } V^2 = 2 c_d^2 g \Delta H \qquad \text{Equation 6}$$

An equation for flow rate Q may be obtained by multiplying the cross sectional area A of flow path by the flow speed V in Equation 6, but for convenience, the overall flow rate coefficient is defined as in Equation 7 below comprehensively for the constants $C_T$, and then, the following Equation 8 is obtained for the flow rate Q.

$$C_T = c_d A \sqrt{2g} \qquad \text{Equation 7}$$

$$Q = C_T \sqrt{\Delta H} \qquad \text{Equation 8}$$

Meanwhile, Equation 6 above is summarized into the following Equation 9 for the water level difference, which is then compared with Equation 2. Then, the flow rate coefficient $c_d$, is represented as in the following Equation 10.

$$\Delta H = \frac{1}{2g} \frac{V^2}{c_d^2} \qquad \text{Equation 9}$$

$$f \frac{L}{D} = \frac{1}{c_d^2} \text{ or } c_d = \sqrt{\frac{D}{fL}} \qquad \text{Equation 10}$$

From Equations 7 and 8, the flow rate Q is proportional to the square root of the water level difference varying depending on the installation state of the infusion solution set 2 and proportional to the overall flow rate coefficient. Further, the flow rate Q is proportional to the square root of the pressure difference.

Here, the water level difference (or pressure difference) varies depending on the installation state of the infusion solution set 2.

Overall flow rate coefficient $C_T$ is a variable determined by the cross-sectional area A of the flow path and the length L of the flow path as verified from Equations 7 and 10 and is thus varied as the manipulating unit 41 of the infusion solution flow rate controller 40 is manipulated. That is, depending on the display gradation to which the manipulating unit 41 of the infusion solution flow rate controller 40 is adjusted, the overall flow rate coefficient $C_T$ may be determined to vary flow rate.

As shown in Equation 8, the overall flow rate coefficient $C_T$ is a variable normalizing the relation between water level difference and flow rate, and thus, if the flow rates for different water level differences are measured at each display gradation 42 of the infusion solution flow rate controller 40, the overall flow rate coefficient $C_T$ for each display gradation may be obtained. As the overall flow rate coefficient at each display gradation is known, if the water level difference is given, the flow rate at the corresponding gradation may be calculated, and if the flow rate at the corresponding gradation is measured, the water level difference may be calculated.

Accordingly, Equation 8 above may be used as the equation Q=f(C,X) used according to the present invention.

FIG. 7 illustrates a graph of flow rate for display gradations according to the result measured by varying the display gradations for each water level difference for a commercial infusion solution flow rate controller and a graph for the overall flow rate coefficient for the display gradations. Here, the solid lines denote the respective flow rates measured for different water level differences, and the dotted lines denote the overall flow rate coefficients calculated using the water level differences and flow rates. The water level difference changed to 72 cm, 101 cm, 150 cm, and 199 cm, and the flow rate was measured for each display gradation, and the water level difference and the flow rate were input to Equation 8 to produce the overall flow rate coefficient.

However, it can be seen from Equation 7 that the overall flow rate coefficient does not converge for the same display gradation. This means that, unlike expected from the theoretical interpretation, the flow rate for water level difference is not normalized to the overall flow rate coefficient and that Equation 8 cannot be used as the equation Q=f(C,X) for the commercial infusion solution flow rate controller.

However, it should be noted here that Equation 8 is a general equation for pipe turbulent flows and that different representations are made for laminar flows.

It can be seen that although the Moody chart shown in FIG. 6 is the graph of friction factor f for Reynolds number Re represented in the following Equation 11, it is divided into three zones depending on the size of Reynolds number Re. That is, the zone where Reynolds number Re is about 2300 or less is separated as a laminar flow zone, and the zone where Reynolds number Re is more than 2300 is separated as a transitional or critical zone or turbulent flow zone.

$$\mathrm{Re} = \frac{\rho D V}{\mu} = \frac{DV}{v} \quad \text{Equation 11}$$

As per Equation 11 above, although Reynolds number is proportional to the flow speed V, the friction factor f in the turbulent flow zone is close to horizontal nearly regardless of the Reynolds number as shown in the Moody chart of FIG. 6 and becomes a constant value regardless of flow speeds.

In other words, if the infusion solution whose flow rate is adjusted by the infusion solution flow rate controller 40 is a turbulent flow, it does not raise a problem to use Equation 8 as the equation Q=f(C,X).

However, given that the commercial infusion solution flow rate controller 40 has a narrow flow path and that the infusion solution has a predetermined degree of viscosity, the flow inside the flow path is highly likely to be a laminar flow, and the Reynolds number Re obtained by Applicant for the commercial infusion solution flow rate controller 40 could be identified to be a tiny value, about 60, which is much smaller than 2300 for determining whether the pipe flow is a laminar flow. That is, the flow of infusion solution in the infusion solution flow rate controller 40 of the commercial infusion solution set is determined to be a fully laminar flow.

In the laminar flow zone, the friction factor f is represented as in Equation 12 below as indicated in the Moody chart of FIG. 6.

$$f = \frac{64}{\mathrm{Re}} = 64 \frac{v}{DV} \quad \text{Equation 12}$$

That is, in the laminar flow zone, the friction factor f is not a constant but is inversely proportional to the Reynolds number Re, wherein the Reynolds number Re is proportional to the flow speed, and thus, the friction factor f is inversely proportional to the flow speed.

Equation 12 for laminar flow and Equation 10 for flow rate coefficient are put in Equation 6 for flow rate, yielding Equations 13 and 14 summarized below.

$$V^2 = 2c_d^2 g \Delta H = 2\left(\frac{D}{fL}\right) g \Delta H = \frac{1}{32}\left(\frac{VD^2}{vL}\right) g \Delta H \quad \text{Equation 13}$$

$$V = \frac{g}{32}\left(\frac{D^2}{vL}\right) \Delta H \quad \text{Equation 14}$$

Accordingly, the laminar flow overall flow rate coefficient $C_L$ representing the variables shown in Equation 14 is defined as in Equation 15 below, and then, Equation 16 may be obtained for flow rate.

$$C_L = \frac{gA}{32}\left(\frac{D^2}{vL}\right) \quad \text{Equation 15}$$

$$Q = C_L \Delta H \quad \text{Equation 16}$$

Resultantly, the flow rate of the infusion solution flow rate controller for fully laminar flow is simply proportional to the water level difference as shown in Equation 16 above and thus makes a difference from Equation 8 for the flow rate-water level difference relation for turbulent flows of the form proportional to the square root of the water level difference.

Applicant normalized the above-described result of flow rate measurement experiment for the commercial infusion solution flow rate controller with the laminar flow overall flow rate coefficient newly defined in Equations 15 and 16 above. FIG. 8 is a graph illustrating the above-described result of flow rate measurement experiment and the laminar flow overall flow rate coefficient newly defined. The solid lines denote the flow rate measured for each display gradation at different water level differences, and the dotted lines denote the laminar flow overall flow rate coefficient obtained from the water level difference and flow rate.

It can be seen from FIG. 8 that although the laminar flow overall flow rate coefficient ($C_L$) obtained at each display gradation remains substantially same even when the water level difference differs and that Equation 16 may be thus used as the equation Q=f(C,X) according to the present invention and may apply to the commercial infusion solution flow rate controller 40.

As set forth above, according to the present invention, the equation Q=f(C,X) may be properly selected depending on whether the infusion solution whose flow rate is adjusted by the infusion solution flow rate controller 40 is a laminar flow or turbulent flow.

Meanwhile, the flow rate measured to obtain the results shown in FIGS. 7 and 8 is not the value measured by counting falling drops, but the value obtained by measuring the flow rate of infusion solution discharged from injection needle.

However, in real-life clinical sites, drops are counted to measure the flow rate, which may cause errors. A result of observation revealed that the volume of infusion solution drops varies depending on the dropping speed rather than remaining constant. Applicant measured the drop volume according to the dropping speed in order to obtain the correlation between dropping speed and drop volume.

FIG. 9 is a graph illustrating the number of drops per ml and the drop volume for dropping speed (drop rate) to show that the drop volume varies as the dropping speed varies. Referring to FIG. 9, as the dropping speed (drop rate) increases, the drop volume (ml per drop) generally increases.

Accordingly, in obtaining the flow rate by multiplying the dropping speed by the drop volume in the actually measured flow rate obtaining step S30 of the method for adjusting the optimal target flow rate using the flow rate coefficient of the flow rate controller according to an embodiment of the present invention, the drop volume corresponding to the dropping speed according to the correlation between dropping speed and drop volume exemplified in FIG. 9 should be selected and multiplied with the dropping speed.

FIG. 10 is a graph of variations in flow rate for the display gradation illustrating an example of actual application of a method for adjusting an optimal target flow rate using a flow rate coefficient of a flow rate controller according to an embodiment of the present invention.

FIG. 10 shows a process of discovering a target gradation of the infusion solution flow rate controller 40 to administer infusion solution at the target flow rate when the target flow rate is determined as 80 ml/h according to a prescription of infusion solution treatment. To avoid confusion, the variables at the first measurement are denoted with the subscript 'try,' and the set target value obtained from the variables at the first measurement is denoted as 'set,' for illustration purposes. Comparison is made with the coefficient C using a subscript in the above-described embodiments, showing that $C_1$ is the same as $C_{try}$ below, and $C_2$ is the same as $C_{set}$ below.

Although FIG. 10 illustrates a graph of flow rate obtained as an experimental value at each water level difference 72 cm, 101 cm, 150 cm, and 199 cm and a process for obtaining through approximation using the graph obtained by the experimental values is described, the graph of flow rate for the display gradations obtained by the experimental values need not be used when actually discovering the target gradation in the compensation device for setting an infusion solution flow rate.

In the compensation device for setting an infusion solution flow rate, the value of the coefficient (C, where it is the laminar flow overall flow rate coefficient ($C_L$) experimentally obtained based on Equation 16 $Q=C_L \Delta H$ is stored per display gradation.

First, the manipulating unit 41 was adjusted to the initial gradation 210 indicating the target flow rate 80 ml/h in the infusion solution flow rate controller 40, and then, the flow rate was measured to obtain the actually measured flow rate $Q_{try}$, which is 150 ml/h. Here, although the initial gradation 210 need not be the display gradation where the target flow rate is marked, the display gradation where the target flow rate is marked is used as the initial gradation 210 from a perspective of use convenience and in light that the flow rate value marked as the display gradation of the infusion solution flow rate controller 40, despite having an error as compared with the actual flow rate, approaches the actually measured flow rate. In this process, the target flow rate and the initial gradation are input to the compensation device for setting an infusion solution flow rate by the target flow rate input step S10 and the initial gradation input step S20, and the actually measured flow rate is obtained by the actually measured flow rate obtaining step S30.

Next, according to the per-display gradation coefficient C experimentally obtained and stored in the compensation device 100 for setting an infusion solution flow rate, since the value of coefficient $C_{try}$ corresponding to the initial gradation 210 is 0.977, the value of coefficient $C_{try}$, 0.977, and the value of the actually measured flow rate $Q_{try}$, 150 ml/h, are input to Equation 16 above, and thus, $$\Delta H = \frac{Q_{try}}{C_{try}} = \frac{150}{0.977} = 154 \text{ cm}$$

is obtained (rounded off). That is, contextual variable (here, water level difference) according to the installation state of the infusion solution set $\Delta H$) is obtained. This process is carried out in the contextual variable obtaining step S40.

Referring to FIG. 10, the curve 200 having a value 220 close to the actually measured flow rate, 150 ml/h, at the position 210 of the display gradation where the target flow rate (rendered to be the same as the initial gradation), 80 ml/h, is marked, among the display gradations is $\Delta H=150$ cm, and thus, approximation may be performed using the curve 200 (process ① of FIG. 10).

Next, the water level difference $\Delta H=154$ cm and the target flow rate, 80 ml/h, was put in Equation 16 $Q=C_L \Delta H$ to produce the coefficient (C, here the laminar flow overall flow rate coefficient $C_L$), and thus, as the coefficient C that should be set to obtain the target flow rate, $C_{set}=0.519$. This process is carried out in the coefficient obtaining step S50. Accordingly, the gradation corresponding to $C_{set}=0.519$, i.e., the target gradation, can be discovered, and here, the discovered target gradation is 45 ml/h, and this is output to the output unit 120 in the infusion solution flow rate setting step S60 so that the manipulating unit 41 of the infusion solution flow rate controller is adjusted to the target gradation, 40 ml/h.

Referring to FIG. 10, when the point 230 corresponding to the target flow rate, 80 ml/h, is discovered in the curve 200 $\Delta H=150$ cm selected for approximation (process ② of FIG. 10), the display gradation 240 at this point 230 is 45 ml/h and becomes the target gradation (process ③ of FIG. 10).

As such, the present invention adopts Equation 16 $Q=C_L \Delta H$ for laminar flows and obtains the value of the laminar flow overall flow rate coefficient corresponding to coefficient C $C_L$ for the display gradation of the infusion solution flow rate controller 40 and stores in the compensation device for setting an infusion solution flow rate. Accordingly, the position of the display gradation corresponding to the target flow rate may be discovered from the flow rate value actually measured once at the initial gradation, and thus, the flow rate may be swiftly adjusted.

According to the present invention, since the installation state of the infusion solution set may be known by actually measuring flow rate, an exact display gradation may be discovered reflecting the installation state even without considering the installation state.

<Automatic Infusion Solution Flow Rate Controller>

FIG. 11 is a view illustrating a state in which an automatic infusion solution flow rate controller 300 is mounted in an infusion solution set 2 and used according to an embodiment of the present invention. FIG. 12 illustrates a perspective view (a) of a flow rate sensor 320 and an electromotive device 330 as shown in FIG. 11. FIG. 13 is a view illustrating a configuration of 1o an automatic infusion solution flow rate controller 300 according to an embodiment of the present invention. FIG. 13 illustrates a cross section of the flow rate sensor 320 mounted in the dropping container 10 and a cross section of an electromotive device 330 mounted in the infusion solution flow rate controller 40.

According to an embodiment of the present invention, the automatic infusion solution flow rate controller 300 is mounted in the infusion solution set 2 allowing the infusion solution in the infusion solution bottle 1 to flow through the tube 20 to the injection needle 30 by gravity to administer the infusion solution to the patient. If a target flow rate is input to the automatic infusion solution flow rate controller 300, the automatic infusion solution flow rate controller 300 measures the flow rate of the infusion solution once and manipulates the manipulating unit 41 of the infusion solution flow rate controller 40 to automatically adjust to the target flow rate.

Further, according to an embodiment of the present invention, the automatic infusion solution flow rate controller 300 continues to actually measure and monitor the flow rate after adjusting to the target flow rate, and if the actually measured flow rate departs from the target flow rate, the automatic infusion solution flow rate controller 300 manipulates once the manipulating unit 41 of the infusion solution flow rate controller 40 to be adjusted to the target flow rate.

To that end, the automatic infusion solution flow rate controller 300 includes a flow rate sensor 320 mounted in the dropping container 10 to detect the flow rate of infusion solution flowing through the tube 20, a electromotive device 330 mounted in the infusion solution flow rate controller 40 to adjust the position of manipulation of the manipulating unit 41, and a control device 310 controlling the operation of the electromotive device 330 according to the detected flow rate to adjust the flow rate to the target flow rate.

The flow rate sensor 320 includes a holder 323 that is opened to both sides by a hinge 323a to allow the dropping container 10 to be inserted therein, and after the insertion of the dropping container 10, closed to detachably hold the dropping container 10 and a light emitting device 321 and light receiving device 322 provided in an inner surface of the holder 323. The inner surface of the holder 323 holds and contacts the dropping container 10. The light emitting device 321 emitting light to the held dropping container 10 and the light receiving device 322 receiving light passing through the dropping container 10 are installed on the inner surface of the holder 323. As the falling drop 12 disturbs the received light, the drop is counted depending on whether the received light is disturbed, and the count signal for the drop is transferred to a controller 314 described below. The holder 323 has a window 323b through which the inside of the dropping container 10 may be viewed, allowing the falling drop 12 to be viewed at the raw eye.

The electromotive device 330 includes a holding means detachably holding the infusion solution flow rate controller 40 varying the flow path to adjust the flow rate according to the position of manipulation of the manipulating unit 41 and an electromotive means adjusting the position of manipulation of the manipulating unit 41. According to an embodiment of the present invention, the infusion solution flow rate controller 40 is in such a type as has the manipulating unit 41, which rotates around a vertical axis, at a lower portion of the body 43 and display gradations 42 along the side circumference, and thus, the holding means and the electromotive means are provided to fit such type.

The holding means of the electromotive device 330 detachably holds the infusion solution flow rate controller 40 such that the body 43 does not move and rotatably holds the manipulating unit 41. To that end, the holding means of the electromotive device 330 includes a case 366, a manipulating unit holding part 334 holding the manipulating unit 41 of the infusion solution flow rate controller 40 and supported by the case 336 to be rotatable by a bearing 333 disposed at a lower portion thereof, and a body holding part 335 provided at the case 336 to be disposed at an upper portion of the manipulating unit holding part 334 to hold the body 43 of the infusion solution flow rate controller 40 not to rotate together with the manipulating unit holding part 334 rotating the manipulating unit 41.

According to an embodiment of the present invention, the manipulating unit holding part 334 and the body holding part 335 are structured to allow an object to be held to be inserted therein, and protrusions 41a and 43a are formed on the surface of the object, which is the manipulating unit 41 and the body 43, to prevent slid. Thus, the manipulating unit holding part 334 and the body holding part 335 have grooves 334a and 335b corresponding in shape to the protrusions 41a and 43a formed in the inner surfaces where the object is inserted, so that the protrusions 41a and 43a of the object are fitted into the grooves 334a and 335b in the inner surface.

A hole 336a is formed that sequentially passes through the bottom of the inside of a hole where the manipulating unit 41 is inserted in the manipulating unit holding part 334 and the portion where the manipulating unit holding part 334 is installed in the case 336, allowing the tube (which has an injection needle at an end thereof) connected to a lower portion of the manipulating unit 41 of the infusion solution flow rate controller 40 to pass therethrough and allowing the manipulating unit 41 to be inserted and held by the manipulating unit holding part 334.

The body holding part 335 has a step formed in an inside thereof and is formed in a short C-shaped pipe cut in the longitudinal direction to allow the tube 10 to be inserted and penetrate the inside through the cut portion and allow the body 43 of the infusion solution flow rate controller 40 to be then inserted through its lower inlet and stuck to the step.

The case 336 includes a rail 336b allowing the body holding part 335 to be slidably mounted therein so that the body holding part 335 may be moved in a direction opposite the manipulating unit holding part 334.

By such configuration, the infusion solution flow rate controller 40 may be held in such a sequence as to expand the interval between the body holding part 335 and the manipulating unit holding part 334, insert the manipulating unit 41 of the infusion solution flow rate controller 40 into the manipulating unit holding part 334, and descend the body holding part 335 to the manipulating unit holding part 334 to insert the body 43 of the infusion solution flow rate controller 40 into the body holding part 335.

The electromotive means of the electromotive device 330 is a component to rotate the manipulating unit holding part 334 rotatably provided by the bearing 333 and includes a stepping motor 331 that may adjust the rotational position and rotational angle and a gear 332 that reduces the rotational speed of the stepping motor 331 to rotate the manipulating unit holding part 334. Here, the stepping motor 331 is a motor that may precisely adjust the rotational position and rotational angle according to a pulse signal from the controller 314 as described below and may be replaced with other types of motors that may detect the rotational position and adjust the rotational angle. Of course, such configuration may also be possible where the manipulating unit holding part 334 is directly rotated by a gear installed at the rotating shaft of the stepping motor 331 without the gear 332, and a gear hole is formed along the outer circumferential surface of the manipulating unit holding part 334.

Meanwhile, it is apparent that the holding means and electromotive means of the electromotive device 330 may be changed in structure to be applicable to the infusion solution flow rate controller configured in different types depending on manufacturers as shown in FIG. 2. Further, according to an embodiment of the present invention, although the infusion solution flow rate controller 40 is of a different type, the electromotive device 330 may be manufactured and replaced to fit the type of the infusion solution flow rate controller 40.

For use convenience, the electromotive device 330 is detachably provided in the case of the control device 310, and for such purpose, a latching hole 310a is provided in an outer surface of the case of the control device 310 to detachably couple the electromotive device 330, and although not shown in the drawings, a hook is provided in the case 336 of the electromotive device 330 to be hooked to the latching hole 310a.

The control device 310 includes an input unit 311 for the user's key input, an output unit 312 displaying information to be shown to the user, a memory 313 for storing information, and a controller 314 controlling the electromotive device 330 according to the flow rate detected by the flow rate sensor 320 to automatically adjust the flow rate.

The memory 313 includes characteristic information on the infusion solution flow rate controller 40 and characteristic information on the dropping container 10.

As set forth above, the characteristic information on the infusion solution flow rate controller 40 includes information on the equation $Q=f(C,X)$ previously set among the measurable contextual variable X varying depending on the installation state of the infusion solution set 2, the coefficient C varying depending on the position of manipulation of the manipulating unit 41 of the infusion solution flow rate controller 40, and the flow rate Q of infusion solution administered through the infusion solution set and the value of coefficient C per position of manipulation of the manipulating unit 41 as obtained by putting in the contextual variable X and the flow rate Q in the equation.

Here, the information on the position of manipulation of the manipulating unit 41 corresponding to the value of the coefficient C is information on the display gradation of the infusion solution flow rate controller 40 for output to the output unit 120 and the type of pulse signal for adjusting the rotational position and rotational angle of the stepping motor 331.

According to an embodiment of the present invention, the equation becomes equation $Q=CX$ indicating that the flow rate Q is proportional to each of the contextual variable X and the coefficient C since the infusion solution administered has a laminar flow as described above, and the contextual variable X is constituted of the difference in water pressure or height between the infusion solution bottle 1 and the injection needle 30 as determined according to the installation state of the infusion solution set.

Meanwhile, in case the infusion solution flow rate controller 40 is not of the type shown in FIGS. 11 and 13 but of a different type as exemplified in FIG. 2, the characteristic information on the infusion solution flow rate controller 40 is varied as well. Per-type characteristic information on the infusion solution flow rate controller 40 may be stored and such types may be selectively applied through the input unit 311 so that the present invention may be applicable to various types of infusion solution flow rate controllers 40.

The characteristic information on the dropping container 10, as described above, is information on the drop volume set per dropping speed (number of drops per unit time: number of drops falling for each unit time), and since the characteristic information on the dropping container 10 may differ depending on manufacturers, it needs to be stored to be distinctively selected for each manufacturer. The information on the drop volume is distinctively stored and used per type of the dropping container 10. For example, the information on drop volume is separately stored for a dropping container for adults, discharging 20 drops per 1 cc of infusion solution and a dropping container for infants/children, discharging 60 drops per 1 cc of infusion solution, so that the information on the drop volume of the type selected by the input unit 311 is used upon adjusting the flow rate.

The input unit 311 is provided for additional user manipulation as well as for receiving the target flow rate. Here, the additional user manipulation may include an initialization setting input indicating that the flow rate sensor 320 and the electromotive device 330 are mounted, selection of the type of dropping container 10, selection of the type of infusion solution flow rate controller 40, an input indicating the start of a flow rate adjusting operation after the target flow rate is input, and a reset input for initializing the flow rate adjusting operation.

Upon holding the infusion solution flow rate controller 40 by the electromotive device 330, the initial position of manipulation of the manipulating unit 41 is previously agreed on to be a position where the flow path is closed so that the controller 314 may adjust the rotational position and rotational angle of the stepping motor 331 of the electromotive device 330 based on the initial position of manipulation. Accordingly, if the manipulating unit 41 is not at the position where the flow path is closed when holding the infusion solution flow rate controller 40 by the electromotive device 330, the user should perform the initialization setting input after adjusting the manipulating unit 41 to the position at which the flow path is closed.

The output unit 312 displays information to be shown to the user.

The controller 314 performs an initialization mode, a flow rate adjusting mode, and a flow rate monitoring mode according to an input from the input unit 311.

The initialization mode is a mode in which the user mounts the flow rate sensor 320 in the dropping container 10 and the electromotive device 330 in the infusion solution flow rate controller 40 and then performs the initialization setting input through the input unit 311 and selects the type of infusion solution flow rate controller 40 and the type of dropping container 10.

Upon the initialization setting input, the controller 314 recognizes that the position of manipulation of the manipulating unit 41 is the position where the flow path is closed. Accordingly, the controller 314 recognizes the current position of manipulation as a reference point for moving the position of the manipulating unit 41.

The controller 314 loads, from the memory 313, the characteristic information on the infusion solution flow rate controller and the characteristic information on the dropping container corresponding to the type selected through the input unit 311 in the initialization mode and prepares for the flow rate adjusting mode.

The flow rate adjusting mode is a mode operated as, after the initialization mode, the user inputs a target flow rate through the input unit 311 and makes an input indicating the start of the flow rate adjusting operation.

When receiving the target flow rate in the flow rate adjusting mode, the controller 314 controls the electromotive device 330 to adjust the manipulating unit 41 to a preset initial manipulation position, obtains the actually measured flow rate based on the characteristic information on the dropping container and the flow rate signal sensed through the flow rate sensor 320, obtains the target manipulation position of the manipulating unit 41 based on the actually measured flow rate, and controls the electromotive device 330 to adjust the manipulating unit 41 to the target manipulation position.

Here, since the flow rate signal sensed by the flow rate sensor 320 is a signal obtained by sensing a falling drop, the controller 314 first calculates the dropping speed from the flow rate signal and selects the drop volume corresponding to the calculated dropping speed from the characteristic information and multiplies the selected drop volume with the dropping speed to obtain the actually measured flow rate.

The initial manipulation position is not previously set and may be determined as the position of the display gradation consistent with the target flow rate among the display gradations marked on the infusion solution flow rate controller 40.

The process of obtaining the target manipulation position is performed in such a sequence to put the value $C_1$ of the coefficient C corresponding to the initial manipulation position and the actually measured flow rate obtained at the initial manipulation position in the equation $Q=f(C,X)$ to obtain the value $X_1$ of the contextual variable X, put the value $X_1$ of the contextual variable X and the target flow rate in the equation to obtain the value $C_2$ of the coefficient C, and obtain the manipulation position corresponding to the value $C_2$ of the coefficient C as the target manipulation position.

The control operation of the electromotive device 330 is performed by transferring the pulse signal corresponding to the manipulation position of the manipulating unit 41 to the stepping motor 331.

In the flow rate adjusting mode, the value of the target flow rate input to the input unit 110 and the value of the display gradation corresponding to the target manipulation position among the display gradations marked within the manipulation range of the manipulating unit 41 of the infusion solution flow rate controller 40 are output to the output unit 120 to be confirmed by the user.

As per the flow rate adjusting mode configured above, the flow rate administered through the infusion solution set 2 may be adjusted to the target flow rate by adjusting once the manipulating unit 41 of the infusion solution flow rate controller 40 after actually measuring the flow rate once.

The flow rate monitoring mode is performed after the flow rate adjusting mode, and in this operation mode, a variation in flow as sensed by the flow rate sensor 320 is checked with the manipulating unit 41 adjusted to the target manipulation position corresponding to the target flow rate so as to monitor a difference from the target flow rate.

If the difference between the flow rate sensed in the flow rate monitoring mode and the target flow rate becomes larger than an allowable difference, the controller 314 changes the target manipulation position to adjust the flow rate to the target flow rate. That is, the process of obtaining the target manipulation position is performed with the adjusted target manipulation position take as the initial manipulation position. Specifically, the flow rate sensed at the adjusted target manipulation position and the value $C_2$ of the coefficient C are put in the equation to obtain the value $X_2$ of the contextual variable X, and the value $X_2$ of the contextual variable X and the target flow rate are then put in the equation to obtain the value $C_3$ of the coefficient C, and the electromotive device 330 is controlled to adjust the manipulation position corresponding to the value $C_3$ of the coefficient C to a subsequent target manipulation position.

As such, in the flow rate monitoring mode, although the installation state of the infusion solution set is varied while the infusion solution is administered so that the contextual variable X is changed, the position of the manipulating unit 41 is adjusted once so that the target flow rate is administered, thus allowing the flow rate being administered to remain constant at the target flow rate.

The controller 314 controls the electromotive device 330 to adjust the manipulating unit 41 to the flow path close position in order to terminate administering the infusion solution when receiving a reset input through the input unit 311.

Meanwhile, the controller 314 may also be configured to receive a total amount of infusion solution administered through the input unit 311 and accumulatively add up flow rates sensed by the flow rate sensor 320 while performing the flow rate monitoring mode, and upon reaching the total amount, to adjust the manipulating unit 41 to the flow path close position. Here, instead of the total amount administered, the controller 314 may receive a total time of administration and check the time of administration at the time that the flow rate monitoring mode starts and adjusts the manipulating unit 41 to the flow path close position when reaching the total time of administration.

[Description of symbols]

1: infusion solution bottle
2: infusion solution set
10: dropping container   20: tube   30: injection needle
40: infusion solution flow rate controller 41: manipulating unit 42: display gradation
100: compensation device for setting infusion solution flow rate
110: input unit 120: output unit   130: memory
140: flow rate calculator   150: set value calculator
300: automatic infusion solution flow rate controller
310: control device   311: input unit 312: output unit
313: memory 314: controller
320: flow rate sensor 321: light emitting device 322: light receiving device
323: holder
330: motor   331: stepping motor 332: gear
333: bearing   334: manipulating unit holding part
335: body holding part   336: case

The invention claimed is:

1. An automatic infusion solution flow rate controller, comprising:
a flow rate sensor (320) mounted in an infusion solution set (2) in which an infusion solution flow rate controller (40) varying a flowpath according to a manipulation position of a manipulating unit (41) to adjust a flow rate of an infusion solution is provided in a tube (20), the flow rate sensor (320) detecting a flow rate of the infusion solution; an electromotive device (330) adjusting the manipulation position of the manipulating unit (41); and
a control device (310) controlling the electromotive device (330) to adjust the flow rate, wherein the control device (310) includes:

an input unit (311) receiving a target flow rate;

a memory (313) storing, per manipulation position of the manipulating unit (41), a value of a laminar flow overall flow rate coefficient (C) obtained by putting measured values of a contextual variable (X) and a flow rate (Q) in an equation Q=CX, the contextual variable (X) determined as a water level difference or a water pressure difference varying according to an installation state of the infusion solution set (2), the laminar flow overall flow rate coefficient (C) varying depending on the manipulation position of the manipulating unit (41), and the flow rate (Q) being a flow rate of the infusion solution administered through the infusion solution set (2); and a controller (314), when receiving a target flow rate, controlling the electromotive device (330) to obtain an actually measured flow rate using the flow rate sensor (320) while the manipulating unit (41) is adjusted to a preset initial manipulation position, obtaining a value ($C_1$) of the laminar flow overall flow rate coefficient (C) corresponding to the initial manipulation position and the actually measured flow rate in the equation to obtain a value ($X_1$) of the contextual variable (X) and then putting the value ($X_1$) of the contextual variable (X) and the target flow rate in the equation to obtain a value ($C_2$) of the laminar flow overall flow rate coefficient (C), and controlling the electromotive device (330) to adjust the manipulating unit (41) to a manipulation position corresponding to the value ($C_2$) of the laminar flow overall flow rate coefficient (C), wherein the controller (314), after adjusting the manipulating unit (41) to the manipulation position corresponding to the value ($C_2$) of the laminar flow overall flow rate coefficient (C), checks a variation in flow rate detected by the flow rate sensor (320), and if a difference from the target flow rate becomes larger than a preset allowable difference, puts the detected flow rate and the value ($C_2$) of the laminar flow overall flow rate coefficient (C) in the equation to obtain a value ($X_2$) of the contextual variable (X) and then puts the value ($X_2$) of the contextual variable (X) and the target flow rate in the equation to obtain a value ($C_3$) of the laminar flow overall flow rate coefficient (C), and controls the electromotive device (330) to adjust the manipulating unit (41) to a manipulation position corresponding to the value ($C_3$) of the laminar flow overall flow rate coefficient (C).

2. The automatic infusion solution flow rate controller of claim 1, wherein the flow rate sensor (320) detachably holds a dropping container (10) of the infusion solution set (2), allows light from a light emitting device to pass through the dropping container (10) and to be received by a light receiving device, and counts drops according to whether the light is disturbed by the drops, wherein the controller (314) calculates a flow rate based on the counted drops, and wherein the electromotive device (330) includes a means to detachably hold the infusion solution flow rate controller (40) and adjusts the manipulation position of the manipulating unit (41) under control of the controller (314) while holding the infusion solution flow rate controller (40).

* * * * *